United States Patent [19]

McMickle et al.

[11] Patent Number: 4,484,586
[45] Date of Patent: Nov. 27, 1984

[54] HOLLOW CONDUCTIVE MEDICAL TUBING

[75] Inventors: Robert L. McMickle; James T. Rumbaugh; Robert L. Netsch, all of Spirit Lake, Iowa

[73] Assignee: Berkley & Company, Inc., Spirit Lake, Iowa

[21] Appl. No.: 438,057

[22] Filed: Nov. 1, 1982

Related U.S. Application Data

[63] Continuation-in-part of Ser. No. 382,568, May 17, 1982, abandoned.

[51] Int. Cl.³ .............................................. B29D 23/05
[52] U.S. Cl. ................................... 128/786; 264/165; 156/51; 174/108
[58] Field of Search ............ 128/419 P, 642, 784–786; 174/108, 130, 131 A, 131 B; 156/51; 264/165

[56] References Cited

U.S. PATENT DOCUMENTS

| | | | |
|---|---|---|---|
| 3,485,234 | 12/1969 | Stevens | 128/657 |
| 3,568,660 | 3/1971 | Crites | 128/786 |
| 3,572,344 | 3/1971 | Bolduc | 128/786 |
| 3,585,707 | 6/1971 | Stevens | 29/426.2 |
| 3,760,812 | 9/1973 | Timmet et al. | 174/130 |
| 4,131,759 | 12/1978 | Felkel | 174/131 A |
| 4,135,518 | 1/1979 | Dutcher | 128/419 P |
| 4,172,451 | 10/1979 | Kline | 128/642 |
| 4,369,794 | 1/1983 | Furler | 128/642 |

Primary Examiner—William E. Kamm
Assistant Examiner—Mitchell J. Shein
Attorney, Agent, or Firm—Kinney & Lange

[57] ABSTRACT

A body implantable intravascular lead with a first layer of plastic defining a tube having a precision lumen therein and at least one electrical conductor wrapped helically along the length of one or more plastic layers. The conductors are substantially parallel along the axis at each end for ease of connection to electrodes and the helical wrap of the conductors may vary throughout the length to form a first length having a first flexibility and a second length having a greater flexibility incapable of sustaining the same axial mechanical loading. The conductive wires are overlaid with one or more layers of plastic separately insulating the wires from each other.

8 Claims, 8 Drawing Figures

HOLLOW CONDUCTIVE MEDICAL TUBING

This is a continuation-in-part of co-pending U.S. application Ser. No. 382,568, filed May 17, 1982, entitled "Process for Forming Hollow Tubing" now abandoned.

I. DESCRIPTION

1. Field of the Invention

This invention relates to hollow tubing formed with separately insulated conductors. The tubing is especially adapted for implantation in the human body, particularly for pacemaker leads.

2. Description of the Prior Art

Hollow tubing used in medical devices, such as pacemaker leads and catheters, requires accurate sizing and specialty designs for strength, flexibility and electrical conductance of signals.

Primary requirements of pacemaker leads are that they be fatigue-resistant to a high degree. They must be capable of withstanding constantly, rapidly repeated flexing over a long period of time. The conductor and its insulation must be capable of withstanding repeated lateral and axial flexing without failure producing fatigue. In addition, they must be able to withstand momentary elongation, such as produced by movement of the chest cavity during respiration. Also, when implanted in a youth whose body size will increase, the electrode and lead must be capable of accommodating such growth.

Standard pacemaker leads utilize coiled wire slipped in urethane or silicone tubes as a conductor for pacing. Multi-pacing now requires two or more separate conductors in the lead which requires insulation between the conductors. In most leads, the internal bore of the lead must be open, having a uniform diameter bore, such that a stylet may be readily passed into the lead.

An intravascular catheter is disclosed in Stevens U.S. Pat. Nos. 3,485,234 and 3,585,707. In Stevens, a silver wire is coated with a first plastic extrusion over which a braided wire is laid for strength. A second plastic extrusion overlays the first extrusion binding the braid wires to the extruded plastic layers. The silver wire is pulled at both ends, reducing its diameter, and is removed. A tube is thus formed. The hollow tube has a very uniform internal diameter, and the braid, according to Stevens, provides torsional strength. Although not appreciated by Stevens, the braid could be used as a single conductive lead if the ends were adapted for making electrical contact therewith.

Bolduc U.S. Pat. No. 3,572,344 discloses a lead construction utilizing multiple conductors, commonly known as "tinsel" wire, helically wrapped around a solid core. When used as a pacemaker lead, no stiffening stylet is necessary due to the solid core. Bolduc's apparatus is sufficiently rigid for intravascular insertion.

Dutcher U.S. Pat. No. 4,135,518 discloses a body implantable lead and electrode that employs a coiled conductor within the lumen of a nonconductive tubing and a section of the length contains tinsel wire formed with a hollow core. A stylet may then be inserted into the bore of the lead to facilitate implantation. The tinsel wire section abuts the heart muscle and is free from axial mechanical loading forces, thereby lessening trauma to the heart.

New catheters are desired to not only transport air and liquids, but to sense and monitor body functions which will require single or multiple conductors. Pacemaker applications may now include feedback monitoring, pressure transducers and other circuits. Most new lead applications will require multiple insulated conductors with low resistance. However, all of the flexibility and strength requirements of the prior art catheters and pacemaker leads must still be retained.

Braided tube designs, such as Stevens, are not as flexible as desired due to the interlocking opposing helix wires. If more conductors were desired with such a design, a second layer of braid would have to be applied, increasing the size and rigidity of the tubing. Multiple wires of braid would provide unacceptable flex characteristics and would increase the overall diameter, restricting use to larger veins. Connections to electrodes and other devices to the individual braid layers are difficult and may result in short circuiting.

BRIEF SUMMARY OF THE INVENTION

The present invention comprises lead construction having uniform interior wall diameter hollow tubing with multi-filar electrical conductors separately arranged so as to provide multiple conductors, helically wound about the tubing in varying pitch. Such a construction provides easier attachment points for connecting electrodes to the conductors and allows for variation of the flexibility of the completed catheter or pacemaker lead over its length.

The hollow tubing is formed on a continuous core which remains in place during the forming steps. The core material must have relatively high elongation characteristics which allow it to be elongated to accomplish release as will be described hereinbelow. Core material may be metal or non-metal, such as plastic, depending on the cure temperatures or other processing conditions of the material used to form the tubing on the core. A first layer of plastic coats the core after being applied by a cross head extruder or the like. The coating is then quenched, cured or otherwise processed as required by the particular plastic chosen. The coated core is pulled by a capstan drive to a rotor table with a varying number of spools that supply conductive wire. Conductive wires are laid under equal tension upon the coated core with uniform spacing, such that a multiple helix is formed. At selected intervals, the rotor table motor's speed is varied in comparison to the capstan drive speed, changing the pitch of the helices thus formed. In this manner, a length of tubing formed can have varying degrees of flexibility along its length due to the tightness of the coils formed about it. Electrical connections to the ends are also much easier due to the allowance for greater spacing between each conductive wire when the pitch of the helices are steep.

The coated core with conductors in place is passed through a second crosshead extruder or other means to apply a top layer of plastic material. This second plastic layer is then cured or quenched as required by the plastics chosen. Additional layers of plastic and/or conductors may be formed by adding crosshead extruders and/or rotor tables for applying conductors.

Upon completion of the forming of the tube structure with core in place, it is cut into desired lengths with allowance of an additional core length at each end to facilitate core removal. A short length of the tubing material is stripped from each end of these lengths to expose the core material which is then clamped and pulled. As the core material elongates, its cross-sectional area decreases, freeing it from the inner wall of the tubing. The core is then removed by pulling it from the tubing. The tubing inside diameter and finish conform substantially to the core's outside diameter and finish.

The hollow conductive tubing thus formed has a very small cross-sectional area which allows it to travel convoluted courses through veins and to pass through heart valves. Its small diameter allows it to easily pass through veins without excessive stretching and to pass through heart valves without causing damage to the tissue. Multiple conductors are available, each separated from the other by the overlying plastic coat, which serves as an insulation material. The redundancy required in medical applications can be easily provided by the multiple conductors thus formed. For example, if two conductors are needed, eight may be formed creating a redundancy factor of four times.

As already pointed out, tubing thus formed has a very uniform bore. Tolerances as close as ±0.0001 inch may readily be achieved. An accurate inner diameter allows a smaller stylet to be used in positioning the lead or catheter in the body. A smaller stylet, in turn, means that the entire lead itself can be of smaller cross-sectional area. Another advantage of the tubing thus formed is that its axial mechanical loading charactertistics can vary over the length of the tubing as desired. For example, by varying the pitch of the conductor helix, tubing can be formed such that it is stiffer at one end and more flexible on the other end. Other variations along the length may be provided as desired. This is a distinct advantage as seen in U.S. Pat. No. 4,135,518 to Dutcher, which is incorporated herein by reference.

The helical winding of the conductors provides optimal strain distribution, permits elongation and allows multiple conductor placement on a single layer. Multiple conductor tubing based on the Stevens patents would be very bulky in comparison, having layer upon layer of insulation with braided material in between each layer. Such a construction would be unacceptably thick and would be stiff throughout its length.

Still another advantage of the present invention is that, by varying the pitch of the helices, a length of tubing may be formed whereby the conductors are substantially parallel at each end of the tubing length. Electrical connections at each end are made easier due to the fact that each conductor is spaced further apart from the other than in a helix.

BRIEF DESCRIPTION OF THE DRAWINGS

The detailed description of the invention including a preferred embodiment is hereinafter described with specific reference being made to the drawings in which.

DETAILED DESCRIPTION OF THE INVENTION

Figure 1:
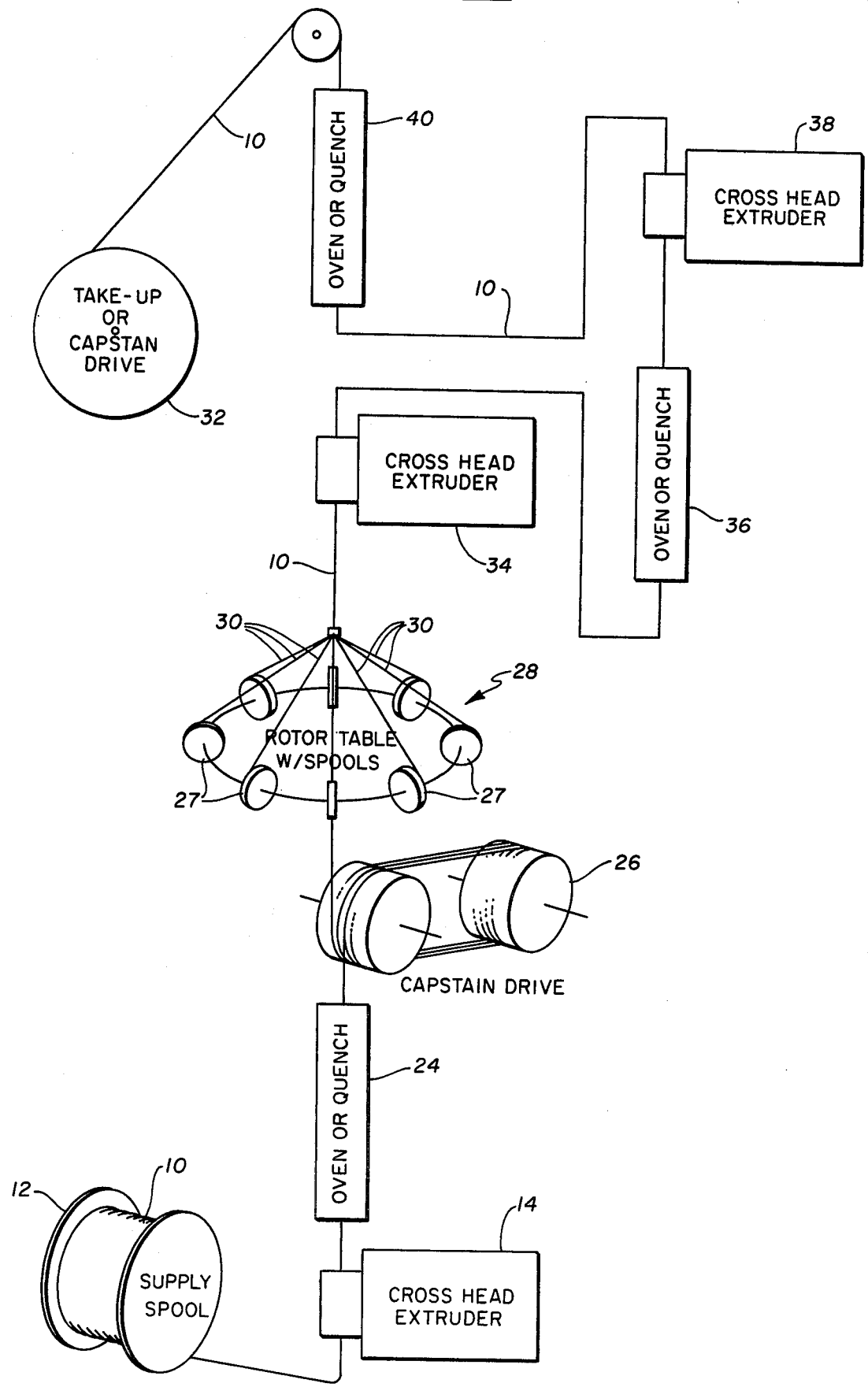
FIG. 1 is a schematic diagram of typical equipment used in the various steps involved in producing hollow conductive tubing according to the present invention.

Referring to FIGS. 1 through 7, core wire 10 composed of annealed copper wire is fed from supply spool 12 to crosshead extruder 14 where core wire 10 receives a coating 13 of body compatible polyurethane, such as the polyether urethane under the trademark PELLETHANE ®, CPR ® 2363-80AE from the Upjohn Company, an organo-silicon polymer, such as that sold under the trademark SILASTIC ® sold by Dow Corning Corporation, or any other suitable nonconductive plastic. Other coating materials may be used, but the named coatings are preferred. The structure and operation of crosshead extruders are well known in the plastic forming art and need not be described in detail herein. Core wire 10 enters a crosshead extruder 14 and a guider tip 16 (shown in FIG. 2) which is surrounded by a heated head block 18 into which the molten plastic material is fed. The fluid plastic entering at port 19 from an extruder pump is extruded as a small tube from a reservoir cavity 20 over guider tip 16 and core wire 10 and is drawn onto wire 10 as indicated generally in FIG. 2A by the running speed and the melted viscosity of the fluid plastic. A vacuum attachment 21 may be used for the draw-down of fluid plastic to core wire 10. Faceplate 22 draws down the outside diameter of first coating 13 on wire core 10 as it exits the extruder. The coated core wire then passes through a cold-water quench or oven 24 into a capstan drive 26.

Figure 2:
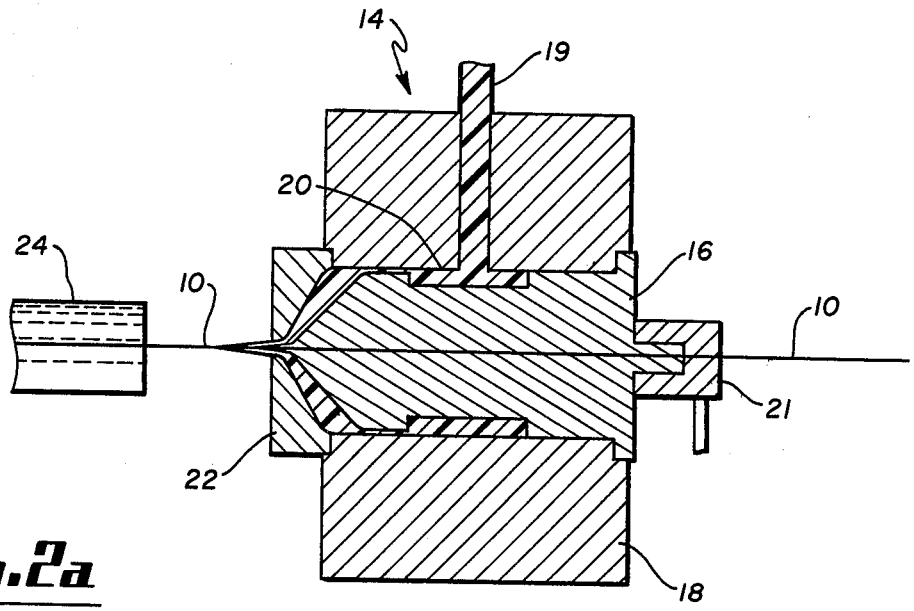
FIG. 2 is a schematic cross-sectional view of a crosshead extruder with crosshead die and core material in place, with a showing of an enlarged portion 2A.
Figure 2A:
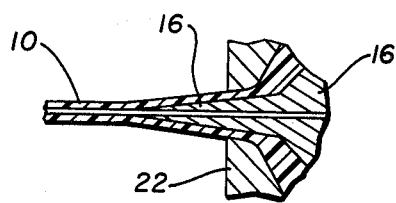
Figure 3:
FIGS. 3 and 4 demonstrate schematically the cross-sectional area change in the core during the elongation/release step.
Figure 4:
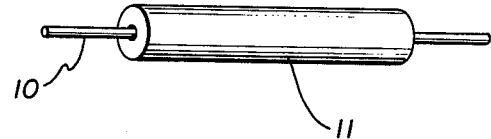
Figure 5:
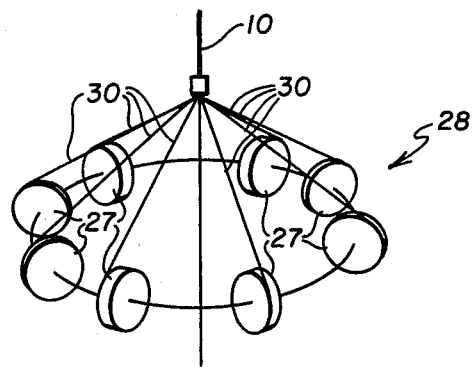
FIG. 5 is an enlarged view of the rotor table of FIG. 1 with eight spools and two spacing gaps.
Figure 6:
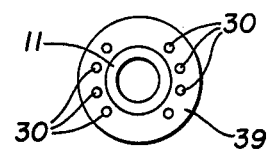
FIG. 6 is an end view of the body implantable lead of the example.
Figure 7:
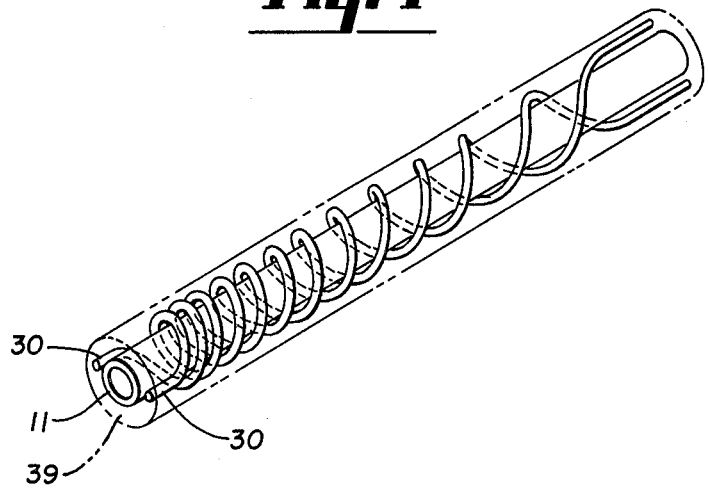
FIG. 7 is a perspective view of the body implantable lead of the invention formed with two conductors.

Rotor table 28 is divided into spaced segments with spools 27 of conductive wire 30 mounted thereon. Equal tension is applied to all spools 27 by means of a regulated air supply through a rotary air joint in rotor table 28 and through a manifold to piston brakes (not shown) at each spool. Each spool 27 on the rotor table 28 supplies a separate conductive wire. In FIG. 1, eight spools 27 are shown in equally spaced segments on the rotor table 28. Wires 30 are preferably made of corrosion resistant, electrically conductive material, e.g. platinum or platinum iridium alloy, a metal oxide, stainless steel or a carbon compound. Preferred wire types are platinum iridium alloys, DBS wire of Fort Wayne Metals, and the medical industry wire designated MP35. All eight conductive wires may initially be taped to the coated core with thin film tape (not shown) to anchor the conductive wires to the coated core. Polyethylene terephthalate sold under the trademark MYLAR ®, 0.002 inches thick, is a suitable tape for this purpose. The tape secures conductive wires 30 to the coated core at the start-up of the winding run. During the run, additional tape is not needed since tension can be maintained after the ends of the conductive wires 30 are fixed by the tape.

As the rotor table 28 revolves, conductive wires 30 are wrapped about the coated core in a helical manner. The pitch of the multiple helices formed by the conductive wires being wrapped on the coated core by rotor table 28 is varied in operation as desired. An electromechanical clutch means can be used to disengage the table while the capstan drive is still operating. Wires 30 would then be laid in a parallel, rather than helical, arrangement. A preferred form is to have the motor for the rotor table 28 and the capstan drive 26 synchronized. The motor for the rotor table 28 can then be slowed or even stopped as desired to alter the pitch of the helix wrapping as formed while the core or capstan drive 26 is continually kept on.

Body implantable leads used in pacemaker lead applications require great flexibility and the distal end that contacts the heart muscle must be incapable of sustaining an axial mechanical load. As noted in Dutcher, U.S. Pat. No. 4,435,518, scarring of heart tissue is lessened when the distal end of the lead is very flexible and incapable of sustaining a great axial mechanical force on the tissue. The proximal end of the lead, usually attached to the wall of the chest, may not require the same axial characteristics. In the process according to the present invention, the axial torque characteristics can be varied at either end of the lead or at desired locations along the length of the lead.

These desirable characteristics are obtained in the present invention by varying the pitch of the conductor wrap. Each end of the body implantable lead will have conductors substantially in parallel formed when the rotor table 28 is stopped. Attachment of the lead to electrodes or other devices is made easier due to the increased separation of each conductor wire 30 from the other. At the distal end of the lead, the rotor table 28 revolves quickly, laying down a wrap of conductive wires 30 with little pitch to the helix formed. This coil region is very flexible and is incapable of sustaining a great axial mechanical force on tissue. In areas along the lead where greater force tolerance is desired, rotor table 28 rotates slower, laying a wrap with a greater pitch and forming a less flexible lead segment with a greater axial mechanical force capability.

A take-up or capstan drive 32 may be connected to the coated and conductive wire at this point. Take-up 32 may include a level wind means (not shown) and torque motor (not shown) to maintain the tension on conductive wires 30 and pull the coated core through the manufacturing procedure as is known in the art.

A gap between each conductive wire 30 is formed by the separation of the spools on rotor table 28 and varies dependent on the speed of capstan drive 32 to the rotational rate of rotor table 28.

The conductive wires and coated core now may be directed to enter a crosshead extruder 34 which is a piston extruder supplying a plastic coating compatible with the first layer. A preferred procedure is to coat with the same plastic as was used in the first coating selected from the coatings listed above. The outer coating 39 then passes through an oven or quench 36 as required by the plastic chosen. Crosshead extruder 38 and oven or quench 40 are next shown in FIG. 1 to illustrate the option for further in-line multiple coatings.

When multiple coatings are utilized, attention must be made to their selection to assure mutual compatibility. For example, a subsequent plastic coating must not be selected which has a higher melting temperature than that of a previous coating, unless special precautions are made in processing.

The coated core wire structure is taken up by take-up 32 which also provides tension and pulling of the structure, i.e, the coated wire during the process, as previously described.

The coated core wire structure is then cut to any predetermined desired length plus an additional amount, for example, one inch. One-half inch of coating, for example, is stripped from both ends of core wire 10 and discarded, shown schematically in FIGS. 3 and 4. The clamping means (not shown) is attached to one end of the exposed core wire 10 while the other end is anchored or otherwise held. The clamp is pulled to cause the core to elongate, for example, to about 80% of its ultimate elongation. The core 10 may be pulled from both ends by a pair of movable clamps also. In either event, the result is the same, i.e., both of the core ends are pulled apart simultaneously to cause elongation of the core. As core wire 10 stretches upon elongation, it diminishes in cross-sectional area and releases internally from the coating material 11. See FIG. 4. This allows coated material 11 to be easily separated from stretched core wire 10, thus providing hollow body implantable leads.

Using wire-forming technology, an annealed copper corewire 10 has dimensional tolerance of ±0.0001 inches. As a finished product, tubing prepared as described hereinabove will have an inside diameter with the same polish and dimensional precision of the copper wire core. The resultant tubing would have a very uniform internal lumen which allows the use of a smaller diameter stiffening stylet to be used. That, in turn, allows construction of a smaller overall diameter body implantable lead which is desirable when the leads must pass into very small veins or arteries.

Core materials should generally exhibit elongation on the order of about 5–35%, depending on the characteristics of the first coating 11 applied to the core 10. In order to release the tubing when the core is stretched, characteristics such as adhesion, hardness and friction must be considered in selecting core material and first coating. Aluminum, copper and nylon are well suited as core materials for use with this invention. Other materials will be readily apparent to those familiar with this art. Various geometric cross-sectional shapes are well suited for this process, such as square, triangular, oval, crescent-shaped and a variety of other shapes. All such core materials are referred to herein generally as a "core" or "core wire" which is meant to mean an elongatable core member. Fluoropolymer coated core wire may be used to enhance release of the core from the first coating. Two methods of release are then available: (1) remove coated core in one step; or (2) remove core and fluoropolymer coating as separate steps.

Generally, no release agent is necessary. A release agent may be used if needed with any particular tubing and core wire material combination chosen. Fluoropolymer coating, as already stated, on a core wire is an example of a suitable release agent. The polymer and wire core may be pulled together or separately in the release and removal step. The number of spools 27 and conductors 30, as well as the dimensions and materials, will vary depending upon the desired application of the lead.

SPECIFIC EXAMPLE

Core 10 is coated in a standard crosshead extruder 14. The thickness of coating will be the total thickness specified for the inner layer of the tube. This example uses annealed copper core 0.028 inches in diameter. It is coated with the organo-silicon polymer sold under the trademark SILASTIC ® to a diameter of 0.038 inches. This makes the plastic coating 11 0.005 inches thick. Out of the crosshead extruder this material is taken-up on capstan drive 26. At this point the material looks the same as a jacketed copper electrical wire. This material can be run any number of times through a crosshead extruder or in line multiple extruders if so elected. A regular tube without the core could collapse from the pressure of the crosshead extruder. Thoses pressures typically run up to 4000 psi. As long as melt points do not conflict, any number of different materials may be layered.

The coated core from extruder 14 and oven 24 is strung onto capstan drive 26, run through rotor table 28, crosshead extruder 34, oven or quench 36 and on to take-up 32. Crosshead extruder 38 and oven quench 40 are shown to illustrate in line multiple coating. Rotor table 28 has eight spools of 0.004 inch diameter stainless steel wire. The table is divided into ten equally spaced positions, with two groups of four spools separated by two gaps left in table 28. Equal tension is applied to all eight spools by means of a regulated air supply passing through a rotary air joint (not shown) in the table through a manifold to piston brakes (not shown) at each spool. Any number of spools will work. For example, up to fourteen have been used. Wire as small as 0.001 inch diameter has been used. All eight wires are taped to the coated core with thin film tape e.g., Mylar 0.002 inches thick. Take-up 32 includes a level wind means and torque motor (not shown). Capstan drive 26 and rotor table 28 are mechanically linked through a quick change gearbox (not shown) driven by a common motor (not shown). A DC constant torque motor with a line regulated solid state speed controller is satisfactory. Many other drive means are acceptable such as a motor for the capstan drive 26 and a separate motor for the rotor table 28 with appropriate feedback to hold a precise relationship between the two.

When producing pacemaker leads of a twenty-four inch length, the rotor table motor is stopped until over one inch of core material has passed the table. The rotor table is then started and run until twenty-four inches of core material have passed and the table is stopped again until over one inch of core material passes through the table. The process continues, such that twenty-four inch segments of pacemaker leads are formed, each having one inch on each end of conductor wires in parallel, rather than a coil shape. This maximizes the separation between the conductor wires to allow electrodes or other devices to be more easily connected. The pitch of the helices formed by the conductors can also be varied in each twenty-four inch section by merely altering the speed of the rotor table.

In forming a body implantable lead with varying flexibility, the rotor table moves quickly for the first four inches following the formation of the one inch and segment. The conductor wires 30 are wrapped in a tight coil with approximately a 0.004 inch gap between each wire. The rotor table 28 is then slowed such that the conductors are wrapped in a helix of greater pitch, with about a 0.012 inch gap between each wire. The second end is run as described above with the rotor table stopped. The lead thus produced has a greater flexibility at the tightly coiled end than the more loosely coiled segment. The tighter coils have a low axial mechanical force and are used as the distal or heart end of pacemaker leads. The more loosely coiled end has a higher axial mechanical force resulting in a stiffer lead which can be used as the proximal end of a pacemaker lead.

The conductor wound coated core now enters crosshead extruder 34. For this coating 39, organo-silicon under the trademark SILASTIC®, a thermal cure material, is used. The finished diameter will be 0.056 inches. From crosshead extruder 34, the core enters oven 36 to cure the initial layers of plastic. If the coating was a thermal plastic, a screw type extruder would be used, and a quench trough would be used in place of oven 36. From the oven, the finished tube structure is taken up on the take-up 32 and the tube is ready to be cut to length and the core can be pulled as already described.

The finished product, which in this example has been made on a continuous process, has an inside diameter of 0.028 inches and is held as precise as the copper core. Eight 0.004 inch diameter stainless steel wires precisely wound around the 0.038 inch diameter organo-silicon plastic wall and covered with organo-silicon plastic to a diameter of 0.056 inch are included in the resultant composite structure. The internal diameter of the lead has a very uniform lumen which gives precise flex characteristics.

The body implantable lead thus formed has eight separately insulated conductor wires. Two gaps separate the eight wires into two groups of four. This allows the body implantable lead to be used as a two conductor lead with a redundancy factor of four. Attachment of electrodes or other devices to the end of the leads is made easier due to the conductors being substantially parallel at both ends.

In considering this invention, it should be remembered that the disclosure is illustrative only, and the scope of the invention is to be determined by the appended claims.

What is claimed is:

1. A continuous process of forming a plurality of conductive body implantable leads each having a lumen of tight inside dimensional tolerances, comprising the steps of:
   providing a continuous core material;
   extruding a first layer of body-compatible non-conductive plastic material onto the core;
   winding a plurality of electrical conductors on the coated core such that each conductor forms a helix physically separated from each other conductor, the positioning and orientation of the conductors prior to being wound onto the coated core being evenly distributed about the circumference of the wire thereby to balance the tension forces applied to the structure as the conductors are wound;
   extruding a coating over the electrical conductors and said coating with a second coating of body-compatible non-conductive plastic material, said second coating being compatible with said first coating and electrically insulating the individual conductors of such helix from each other;
   cutting the coated and conductive core material into lengths; and
   removing the core material from the first layer of plastic material.

2. The process of claim 1 wherein the winding of said electrical conductors varies in pitch along each length of lead such that said conductors are substantially parallel at the ends of the length of said lead.
   varying the pitch of the helices formed by the electrical conductors at predetermined locations along the length of the coated core wire such that the conductors are substantially parallel at the ends of each length so as to be at a maximum physical separation from each other, and winding the conductors relatively tighter at one end of the length than the other end forming a length with greater flexibility at the tight end than the other end;
   coating an additional layer of a body-compatible non-conductive plastic material onto the conductive coated core wire by means of a crosshead extruder and curing or quenching as required;

cutting said coated core wire into discrete lengths;
pulling both ends of said core wire simultaneously to elongate said core wire reducing its cross-sectional area freeing it from said plastic coating; and
removing said core wire from said plastic coating to provide hollow body implantable leads.

3. The process of claim 1 wherein the winding of said electrical conductors is varied at predetermined locations along the length of the lead whereby varying flexibility characteristics are imparted to the length of said lead.

4. The process of claim 1 wherein said electrical conductors are initially held in place on the coated core material by a thin film tape.

5. The process of claim 4 wherein said thin film tape is composed of polyethylene terephthalate.

6. The process of claim 1 wherein said electrical conductors are corrosion resistant.

7. The process of forming conductive body implantable leads with a lumen of tight inside dimensional tolerances comprising the steps of:
extruding a continuous core wire of predetermined cross-sectional shape with a body-compatible non-conductive plastic material by means of a crosshead extruder;
quenching or curing the plastic as required;
winding a plurality of electrical conductors on the coated core wire such that each conductor forms a helix about the coated core wire physically separated from each other and extending along the length thereof;
varying the pitch of the helices formed by the electrical conductors at predetermined locations along the length of the coated core wire such that the conductors are substantially parallel at the ends of each length so as to be at a maximum physical separation from each other, and winding the conductors relatively tighter at one end of the length than the other end forming a length with greater flexibility at the tight end than the other end;
extruding an additional layer of a body-compatible non-conductive plastic material onto the conductive coated core wire by means of a crosshead extruder and curing or quenching as required;
cutting said coated core wire into discrete lengths; and
removing said core wire from said plastic coating to provide hollow body implantable leads.

8. A method for manufacturing lengths of tubing having multifilar longitudinally extending helices surrounding a dimensionally controlled inner lumen therein, the method comprising the steps of:
supplying a continuous strand of base wire from a wire dispenser;
extruding a first layer of a plastic material over the base wire to form a coated tube;
supplying a plurality of continuous filaments from a plurality of filament dispensers positioned at equally spaced intervals around a rotor table;
connecting each of the filaments to the coated tube;
transporting the coated tube at a first rate along a transport path through the center of rotation of the rotor table while rotating the rotor table about the transport path at a first rate to wrap the plurality of filaments into a plurality of helices, each of which is in spaced relation to the adjacent helices;
extruding a second layer of a plastic material over the first layer and the filaments;
cutting the material into lengths of tubing; and
removing the base wire from each of the lengths of tubing to form the inner lumen.

* * * * *

UNITED STATES PATENT AND TRADEMARK OFFICE
CERTIFICATE OF CORRECTION

PATENT NO. : 4,484,586

DATED : November 27, 1984

INVENTOR(S) : Robert L. McMickle; James T. Rumbaugh; Robert L. Netsch

It is certified that error appears in the above-identified patent and that said Letters Patent is hereby corrected as shown below:

column 8, delete line 56 through 68.

column 9, delete line 1 through 6.

Signed and Sealed this

Eleventh Day of June 1985

[SEAL]

Attest:

DONALD J. QUIGG

Attesting Officer  Acting Commissioner of Patents and Trademarks